United States Patent
Stewart (10) Patent No.: US 10,653,331 B2
(45) Date of Patent: May 19, 2020

(54) ELECTRODE SENSOR

(71) Applicant: Konan Medical USA, Inc., Irvine, CA (US)

(72) Inventor: Charles Wm. Stewart, Laguna Beach, CA (US)

(73) Assignee: Konan Medical USA, Inc., Irvine, CA (US)

(*) Notice: Subject to any disclaimer, the term of this patent is extended or adjusted under 35 U.S.C. 154(b) by 300 days.

(21) Appl. No.: 15/604,146

(22) Filed: May 24, 2017

(65) Prior Publication Data

US 2017/0340232 A1 Nov. 30, 2017

Related U.S. Application Data

(60) Provisional application No. 62/340,747, filed on May 24, 2016.

(51) Int. Cl.
| | |
|---|---|
| *A61B 5/0408* | (2006.01) |
| *A61B 5/0416* | (2006.01) |
| *A61B 5/0478* | (2006.01) |
| *A61B 5/0492* | (2006.01) |
| *A61B 5/0496* | (2006.01) |
| *G01N 27/04* | (2006.01) |

(52) U.S. Cl.
CPC ........ *A61B 5/04087* (2013.01); *A61B 5/0408* (2013.01); *A61B 5/0416* (2013.01); *A61B 5/0478* (2013.01); *A61B 5/0492* (2013.01); *A61B 5/0496* (2013.01); *A61B 2560/0468* (2013.01); *A61B 2562/0209* (2013.01); *A61B 2562/0215* (2017.08); *A61B 2562/125* (2013.01); *G01N 27/04* (2013.01)

(58) Field of Classification Search
CPC .................................................. A61B 5/04087
USPC ........................................ 600/391, 392, 394
See application file for complete search history.

(56) References Cited

U.S. PATENT DOCUMENTS

| | | | |
|---|---|---|---|
| 3,830,229 A | 8/1974 | Johnson | |
| 3,993,049 A * | 11/1976 | Kater | A61B 5/04085 600/391 |
| 3,998,215 A * | 12/1976 | Anderson | A61B 5/0408 600/391 |
| 4,327,737 A | 5/1982 | Szpur | |
| 4,383,529 A * | 5/1983 | Webster | A61N 1/044 604/20 |
| 4,417,581 A | 11/1983 | Dawson | |
| 4,515,162 A * | 5/1985 | Yamamoto | A61B 5/04087 600/391 |

(Continued)

FOREIGN PATENT DOCUMENTS

| | | |
|---|---|---|
| EP | 0276661 A2 | 8/1988 |
| JP | 2006-003534 Y2 | 2/1994 |
| WO | 2015028589 A1 | 3/2015 |

OTHER PUBLICATIONS

Hawlina, M. et al., "New noncorneal HK-loop electrode for clinical electroretinography," Documenta Ophthalmologica 81, 1992, pp. 253-259.

*Primary Examiner* — Lee S Cohen
(74) *Attorney, Agent, or Firm* — LaBatt, LLC (57) ABSTRACT

An electrode sensor is provided. The electrode sensor can include a conductive sensor area that is at least partially covered by hydrogel. The hydrogel can be conductive and adhere to skin. A receptacle can form an open container surrounding the conductive sensor area and the hydrogel.

20 Claims, 4 Drawing Sheets

(56) References Cited

U.S. PATENT DOCUMENTS

| | | | |
|---|---|---|---|
| 4,979,517 A * | 12/1990 | Grossman | A61N 1/046 |
| | | | 607/153 |
| 5,154,174 A | 10/1992 | Hawlina | |
| 5,297,554 A | 3/1994 | Glynn et al. | |
| 5,402,780 A * | 4/1995 | Faasse, Jr. | A61B 5/0408 |
| | | | 29/877 |
| 5,560,357 A * | 10/1996 | Faupel | A61B 5/04 |
| | | | 600/345 |
| 5,772,591 A | 6/1998 | Cram | |
| 5,833,622 A * | 11/1998 | Meathrel | A61B 5/04087 |
| | | | 600/511 |
| 7,496,400 B2 | 2/2009 | Hoskonen et al. | |
| 8,332,009 B2 * | 12/2012 | McLaughlin | A61B 5/0416 |
| | | | 600/372 |
| 8,406,843 B2 * | 3/2013 | Tiegs | A61B 5/0416 |
| | | | 600/391 |
| 8,798,710 B2 * | 8/2014 | Chi | A61N 1/0488 |
| | | | 600/396 |
| 9,026,189 B2 | 5/2015 | Garcia et al. | |
| 2007/0282188 A1 * | 12/2007 | Copp-Howland | A61K 33/00 |
| | | | 600/391 |
| 2009/0318793 A1 | 12/2009 | Datta et al. | |
| 2014/0135887 A1 | 5/2014 | Totman et al. | |
| 2014/0142409 A1 | 5/2014 | Garcia et al. | |
| 2014/0323841 A1 | 10/2014 | Odaka et al. | |
| 2017/0319093 A1 | 11/2017 | Stewart | |

* cited by examiner

ELECTRODE SENSOR

REFERENCE TO RELATED APPLICATIONS

The current application claims the benefit of U.S. Provisional Application No. 62/340,747, filed on 24 May 2016, which is hereby incorporated by reference.

TECHNICAL FIELD

The disclosure relates generally to electrode sensors, and more specifically, to an electrode sensor applied dermally which can have a reduced footprint, for collection of electrophysiological electrical energy generated from a multitude of anatomical sites.

BACKGROUND ART

Electrode sensors are generally used to collect electrophysiological signals of patients in a wide variety of electrophysiological testing applications. Electroencephalography (EEG), electrooculography (EOG), electromyography (EMG), facial electromyography (fEMG), electroretinography (ERG), and visual electrophysiology (VEP) are a few examples of electrophysiological testing applications in which electrode sensors are used. In these examples of electrophysiological testing applications, the electrode sensors can collect electrophysiological signals produced from a body structure or structures that are the focus of the particular testing application. For example, in EEG, electrode sensors can collect electrical signals from skin locations adjacent to defined brain locations in response to a stimulation. In EOG, electrode sensors can collect electrical signals from skin locations adjacent eye muscles in response to visual stimuli. In EMG, electrode sensors can collect electrical signals from skin locations adjacent skeletal muscles in response to nervous stimulation. In fEMG, electrode sensors can collect electrical signals from skin locations adjacent facial muscles in response to a stimulation. In ERG, electrode sensors can collect electrical signals from conjunctival, corneal, or skin locations adjacent the retina in response to visual stimuli. Additionally, in VEP, electrode sensors can collect electrical signals from skin locations adjacent the visual cortex in response to visual stimuli. In all of these examples, the electrical signals generated from the various body structures are typically in the micro-volt range with some as small as fractions of a micro-volt. Generally, after some averaging and signal processing, the timing and amplitudes of the electrical signals can be used to monitor and assess the function or dysfunction of particular patient body functions.

A number of electrode sensors are currently available that can be used to collect electrophysiological signals for testing applications such as EEG, EOG, EMG, fEMG, ERG, and VEP. A disposal snap skin electrode is one example of an electrode sensor that is used in electrophysiological testing applications. A disposal snap skin electrode is generally round, oval, or rectangular in form, composed typically of non-conductive, non-woven fabric or synthetic material, and is very low cost.

SUMMARY OF THE INVENTION

This summary of the invention introduces a selection of certain concepts in a brief form that are further described below in the detailed description of the invention. It is not intended to exclusively identify key features or essential features of the claimed subject matter set forth in the claims, nor is it intended as an aid in determining the scope of the claimed subject matter.

Aspects of the present invention are directed to an electrode sensor having a reduced footprint that is suitable for a multitude of electrophysiological testing applications that can include electroencephalography (EEG), electrooculography (EOG), electromyography (EMG), facial electromyography (fEMG), electroretinography (ERG), electrocardiogram (ECG) and visual electrophysiology (VEP). In one embodiment, the electrode sensor can be formed as a receptacle surrounding a conductive sensor area, which can be formed of a hydrogel that serves both as a conductive and adhesive element for the electrode sensor.

A first aspect of the invention provides an electrode sensor comprising: a conductive sensor area; hydrogel at least partially covering the conductive sensor area, wherein the hydrogel is conductive and adheres to skin; and a receptacle forming an open container surrounding the conductive sensor area and the hydrogel.

A second aspect of the invention provides an electrophysiological testing system comprising: a set of electrode sensors, at least one of the set of electrode sensors including: a conductive sensor area; hydrogel at least partially covering the conductive sensor area, wherein the hydrogel is conductive and adheres to skin; and a receptacle forming an open container surrounding the conductive sensor area and the hydrogel; and means for collecting signals corresponding to electrical energy sensed by the at least one of the set of electrode sensors.

A third aspect of the invention provides an electrode sensor comprising: a conductive sensor area; a conductive hydrogel pellet at least partially covering the conductive sensor area, wherein the conductive hydrogel pellet adheres to skin; and a first flange element having a first end affixed near the conductive sensor area and a second end extending away from the conductive sensor area.

A fourth aspect of the invention provides a method of acquiring electrophysiological data from a patient, the method comprising: applying an electrode sensor to the skin of the patient, wherein the electrode sensor includes a conductive sensor area; and hydrogel at least partially covering the conductive sensor area, wherein the hydrogel is conductive and adheres to the skin of the patient. An embodiment of the hydrogel is a conductive hydrogel pellet.

An embodiment of the electrode sensor can include a receptacle forming an open container surrounding the conductive sensor area and the hydrogel. The receptacle can protect the hydrogel from being physically handled or exposed to the atmosphere. To this extent, a user can handle the receptacle when applying or removing the electrode sensor to/from the skin of the patient.

An embodiment of the electrode sensor can include a release plate attached to an open end of the receptacle. The release plate can completely enclose the open container of the receptacle to prevent the hydrogel from being exposed to the atmosphere. The user can remove the release plate prior to applying the electrode sensor to the skin of the patient.

An embodiment of the electrode sensor can include one or more flanges extending from the conductive sensor area. The flanges can be held by a user when applying and/or removing the electrode sensor to/from the skin of the patient.

Once applied to the skin of the patient, the electrode sensor can be used to acquire signal data corresponding to electrical energy sensed by the electrode sensor at the location on the skin of the patient. To this extent, the electrode sensor can be electrically connected to a control unit, which can collect and process the signal data. An embodiment of the electrode sensor can include a snap connector, which can be used to make the electrical connection.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the present invention are directed to an electrode sensor having high flexibility and conductivity that is suitable for a multitude of electrophysiological testing applications that can include electroencephalography (EEG), electrooculography (EOG), electromyography (EMG), facial electromyography (fEMG), electroretinography (ERG), electrocardiogram (ECG) and visual electrophysiology (VEP). In one embodiment, the electrode sensor can be formed as a receptacle surrounding a conductive sensor area, which can be formed of a hydrogel that serves both as a conductive and adhesive element for the electrode sensor.

Figure 1A:
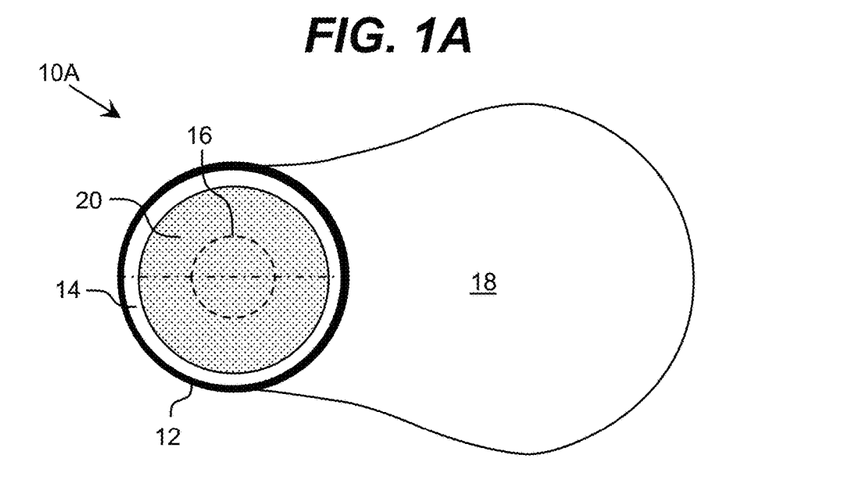
FIGS. 1A and 1B show top views of illustrative electrode sensors according to embodiments.
Figure 1B:
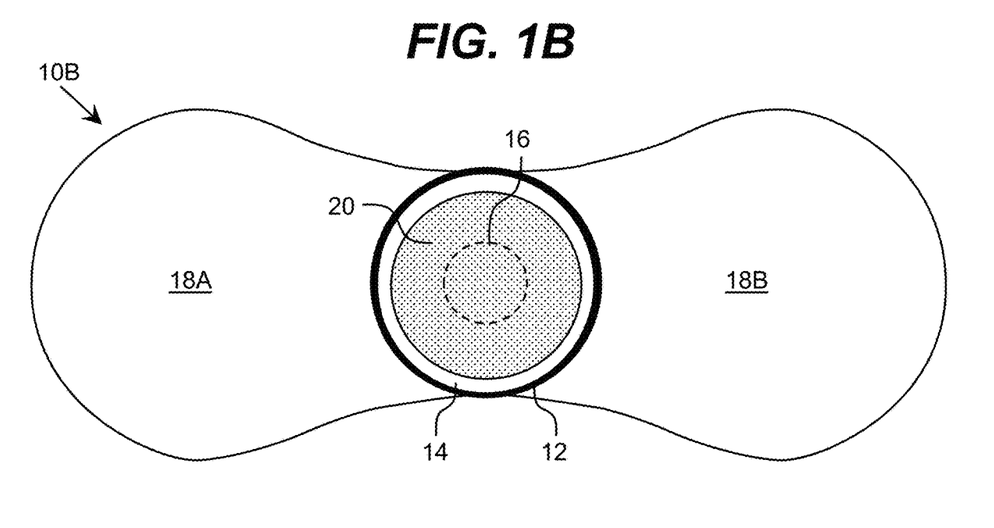
Figure 2A:
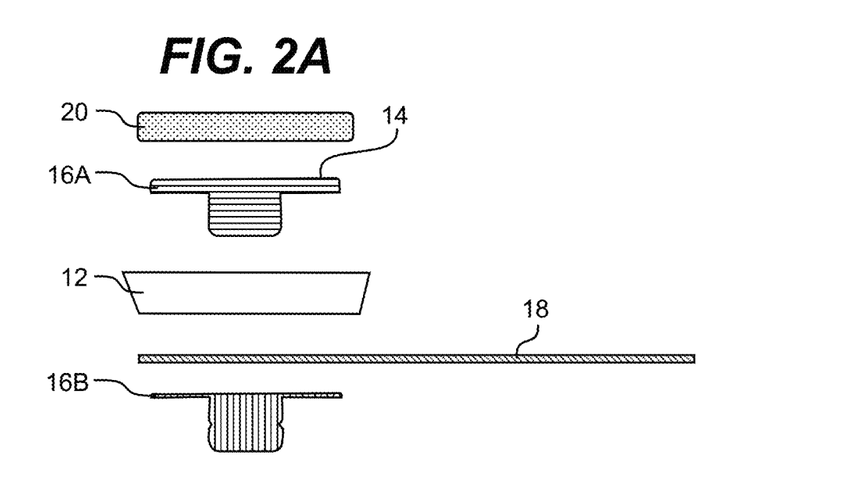
FIGS. 2A and 2B show exploded views of illustrative parts for fabricating electrode sensors according to embodiments.
Figure 2B:
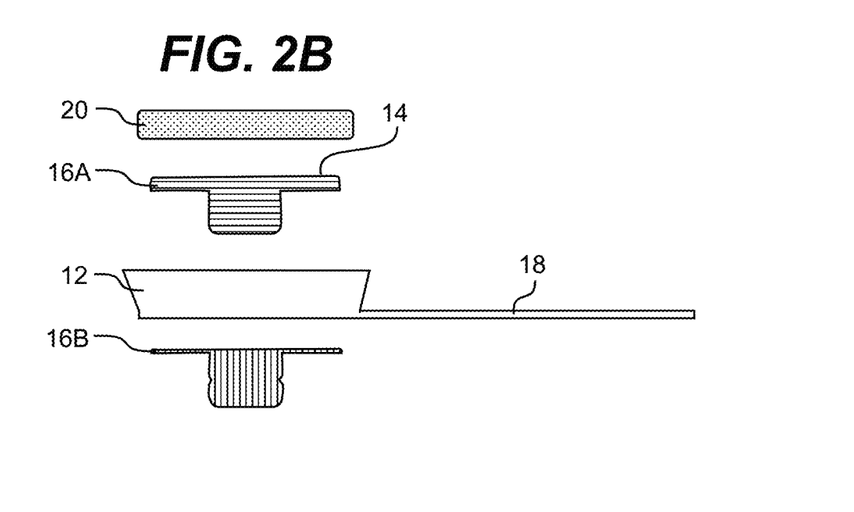
Figure 3A:
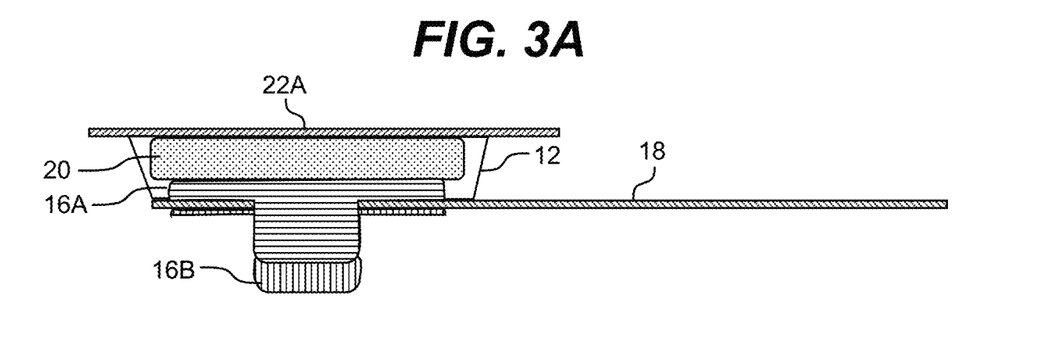
FIGS. 3A and 3B show side cutaway views along the centerline shown in FIG. 1A of illustrative electrode sensors according to embodiments.
Figure 3B:
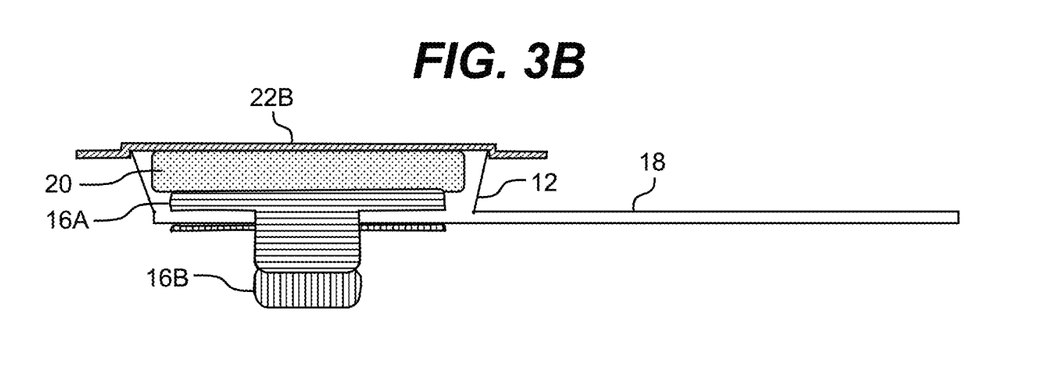

Turning to the drawings, FIGS. 1A and 1B show top views of illustrative electrode sensors 10A, 10B according to embodiments; FIGS. 2A and 2B show exploded views of illustrative parts for fabricating an electrode sensor according to embodiments; and FIGS. 3A and 3B show side cutaway views along the centerline shown in FIG. 1A of illustrative electrode sensors according to embodiments. As illustrated, each electrode sensor 10A, 10B can include a receptacle 12 surrounding a conductive sensor area 14 that is continuous with a connector 16. Additionally, an electrode sensor 10A, 10B can include one or more flange elements 18, each of which extends from a side of the receptacle 12. The conductive sensor area 14 is at least partially covered with a conductive hydrogel pellet 20. Further details are described with reference to the FIGS. 1A-3B.

In an embodiment, the receptacle 12 has a shape of a saucer. In particular, the receptacle 12 can define an elliptical (e.g., circular) area, which has a gradually decreasing cross-sectional area with increasing depth as shown in FIGS. 2A and 2B. However, it is understood that this configuration is only illustrative of various shapes that can be utilized. The receptacle 12 can be formed of a flexible material. Furthermore, the material forming the receptacle 12 can have a low durometer and/or be non-conductive. In an illustrative embodiment, the receptacle 12 is formed of a bio-inert/medical grade silicone rubber. However, it is understood that this is only illustrative and other materials having comparable properties can be utilized to form the receptacle 12.

The conductive sensor area 14 can have a size and shape complementary to the interior region of the receptacle 12. The conductive sensor area 14 can be formed of any type of material configured for collection of electrical energy signals produced from a variety of anatomical sites. As illustrated in FIGS. 2A and 2B, the conductive sensor area 14 can correspond to a conductive surface of a component forming the connector 16. The connector 16 can include any type of connector that is commonly used with electrophysiological devices, such as a snap connector. In this case, the connector 16 can be formed of an eyelet 16A, which includes a conductive surface 14 forming the conductive sensor area 14 and a central portion that is sized to be inserted into a central portion of a stud 16B. The stud 16B can provide a conductive surface to which additional components (e.g., clip/pinch or snap lead wires electrically connected to a control unit) can be attached to receive the electrical energy signals sensed by the conductive sensor area 14.

The snap connector can provide a mechanism for securing other components of the electrode sensor. For example, as illustrated in FIGS. 2A and 2B, the eyelet 16A can extend through a bottom of the receptacle 12 and the flange(s) 18 before being inserted into the stud 16B. In this case, the receptacle 12 and the flange(s) 18 can include an opening sized to allow the eyelet 16A to pass there through, but smaller than the conductive sensor area 14. The components can be kept together through a tight fitting between the eyelet 16A and the stud 16B. In an embodiment, an adhesive, such as glue or the like, can be utilized to permanently attach some or all of the components of the electrode sensor.

Regardless, it is understood that a snap connector is only illustrative of various configurations for an electrode sensor. To this extent, in other embodiments, an electrode sensor described herein can include a metallic disk providing the conductive sensor area 14, which is electrically connected to one end of a lead wire. The opposing end of the lead wire can include a male or female connection point to additional wiring. Additionally, an embodiment of an electrode sensor can transmit a signal representative of the electrical signals sensed by the conductive sensor area 14 using any wireless transmission solution. In this case, a wireless receiver can receive the transmitted signals and provide the signals for processing by a control unit.

In an embodiment, the conductive hydrogel pellet 20 is in the shape of a disc. The conductive hydrogel pellet 20 can be sized to at least partially cover the conductive sensor area 14. In an embodiment, the conductive hydrogel pellet 20 has a size and shape in which it completely covers the conductive sensor area 14. In another embodiment, the conductive hydrogel pellet 20 can have a size and shape such that it completely covers and extends beyond the conductive sensor area 14. Regardless, in an embodiment, the conductive hydrogel pellet 20 is formed of a silver/silver chloride (Ag/AgCl) hydrogel pellet. In this case, the conductive hydrogel pellet 20 can serve as an adhesive and electrical bridge from the skin to the conductive sensor area 14, thereby removing the need to use a conductive paste, such as Ellefix, which typically requires cleanup, such as hair washing, to remove a sticky residue after use.

During use, the conductive hydrogel pellet 20 (e.g., the Ag/AgCl hydrogel pellet) can be placed on an area of patient. The attributes of the conductive hydrogel pellet 20 can have a high conformance to the applied area. The electrode sensor 10A, 10B can be placed anywhere on the skin of a patient from which electrical signals are desired to be acquired. In an illustrative application, the electrode sensor 10A, 10B can be applied to the scalp of a patient. However, it is understood that the electrode sensor 10A, 10B can be utilized in various locations on a patient. Upon application to a desired area, the receptacle 12 can easily morph away from interfering body geometry, such as highly hirsute skin areas, to more fully expose the conductive hydrogel pellet 20 and to be complementary to the morphology of a body structure of the patient.

As shown in FIG. 1A, the electrode sensor 10A can include a single non-adhesive wing-flange element 18. Alternatively, as shown in FIG. 1B, the electrode sensor 10B can include two opposing non-adhesive wing-flange elements 18A, 18B (also generically referred to as a wing-flange element 18). The flange element(s) 18 can be configured to provide medical personnel with an application aid to simplify management of application and/or removal of the electrode sensor 10A, 10B from the skin applied area and/or a connector element. Using the wing-flange element(s) 18 can enable a medical worker to apply the electrode sensor 10A, 10B to a desired location without touching the exposed conductive surface area of the electrode sensor 10A, 10B. This can be particularly useful when the electrode sensor 10A, 10B includes the conductive hydrogel pellet 20, as the wing-flange element can aid in placement and manipulation by avoiding touching and spoilage of the conductive hydrogel pellet 20. Furthermore, in an embodiment, the receptacle 12, and the components included therein, can have a small size thereby making the receptacle 12 inconvenient to handle due to the size.

As illustrated, in an illustrative embodiment, a wing-flange element 18 can have a tear-drop shape and extend to a side of the receptacle 12. Additionally, the wing-flange element 18 can have an area generally matching the intersection of a human thumb and forefinger, with which the wing-flange element 18 can be grasped by a medical worker. While the electrode sensor 10A is shown including a single wing-flange 18 and electrode sensor 10B is shown including a pair of wing-flanges 18A, 18B, it is understood that embodiments can include any number of wing-flanges 18. When multiple wing-flanges 18 are included, the wing-flanges 18 can be spaced evenly about a circumference of the receptacle 12. For example, as illustrated, the electrode sensor 10B can include two wing-flanges 18A, 18B extending from opposite sides of the receptacle 12. Alternatively, the wing-flanges 18A, 18B can have any relative spacing around the circumference of the receptacle 12.

The wing-flange(s) 18 can be formed of any suitable material. In an embodiment, the wing-flange 18 and receptacle 12 are formed of the same material. However, the wing-flange 18 can be formed of other suitable materials. Such materials should not be readily tearable and be capable of withstanding the manipulations described herein. An illustrative material comprises a synthetic material, such as flashspun high-density polyethylene fibers. One such material is Tyvek®, which is sold by E. I. du Pont de Nemours and Company. Regardless, the wing-flange 18 can be permanently secured to the receptacle 12 using any solution, e.g., gluing, mechanical entrapment between the complementary parts 16A, 16B of the connector, and/or the like, which provides a sufficient amount of adhesion for the uses described herein. In an illustrative embodiment shown in FIGS. 2B and 3B, the flange 18 and receptacle 12 can be formed from a single mold.

FIGS. 3A and 3B also show illustrative embodiments of a release plate 22A, 22B, each of which is configured to securely cover the receptacle 12 area and the components located therein, e.g., the conductive surface area 14 and the conductive hydrogel pellet 20. In an embodiment shown in FIG. 3A, the release plate 22A can comprise a planar semi-rigid surface that can be secured to the receptacle 12 using any solution (e.g., an adhesive nature of the exposed surface of the hydrogel pellet, vacuum seal, glue, and/or the like), which enables the release plate 22A to seal off the perimeter of the receptacle 12 and be readily removed from the receptacle 12 when desired. In an embodiment shown in FIG. 3B, the release plate 22B can have shaped depressions complementary to the receptacle 12 to mechanically attach the release plate 22B to the receptacle 12 and seal off the perimeter of the receptacle 12. Inclusion of the release plate 22A, 22B can provide one or more of several advantages including, for example: protection of the conductive hydrogel pellet 20 from dehydration; providing an assembly platform upon which to assemble a connector against the receptacle 12 perimeter supported assembly; provide a sealed package for shipping and handling protection of the conductive hydrogel pellet 20; and/or the like.

Embodiments of the electrode sensor 10A, 10B described herein can be fabricated in any of various sizes. To this extent, the receptacle 12 (and corresponding components located therein) and the wing-flange(s) 18 each can have any of various sizes and shapes. To this extent, the relative sizes of the receptacle 12 and wing-flanges 18 shown are only illustrative and the respective structures can have any of various relative sizes with respect to one another.

In an illustrative embodiment, the electrode sensor 10A, 10B is fabricated to provide a small footprint conductive sensor area 14. For example, the receptacle 12 can have a largest diameter in a range of approximately 10 mm to approximately 20 mm. The smaller diameter of the receptacle 12 can be approximately 10% to approximately 20% smaller than the largest diameter. To this extent, the smaller diameter of the receptacle can be in a range of approximately 8 mm to approximately 18 mm. In a more particular embodiment, the largest diameter of the receptacle 12 is approximately 14 mm and the smaller diameter of the receptacle is approximately 12 mm. In an embodiment, the wing-flange 18 has a diameter in a range of approximately 10 mm to approximately 30 mm. In an embodiment, a total depth of the receptacle is in a range of approximately 1 mm to approximately 5 mm. In a more particular embodiment, the total depth of the receptacle is approximately 1.5 mm.

Figure 4:
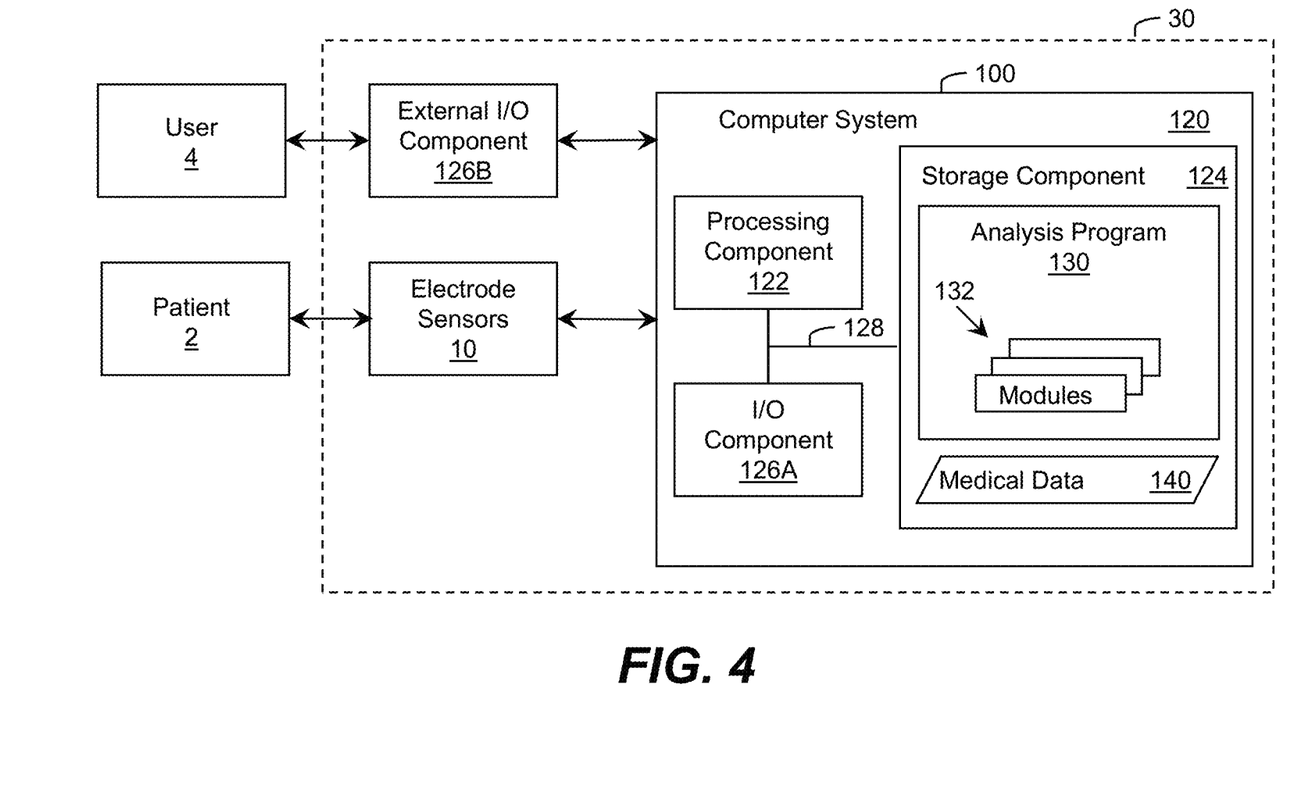
FIG. 4 shows a schematic of an electrophysiological testing system that can include using the electrode sensor described herein according to an embodiment.

FIG. 4 shows a schematic of an electrophysiological testing system 30 that can include using one or more of the electrode sensors 10 (e.g., the electrode sensor 10A and/or the electrode sensor 10B) described herein according to an embodiment. In this embodiment, the electrophysiological testing system 30 can include any computer-based electrophysiological testing system or device that uses electrode sensors to monitor and/or diagnose a patient in real-time. For the purposes of illustrating the interaction of some of the components of the electrophysiological testing system 30, the electrode sensors 10 are illustrated as part of the testing system 30, however, it is understood that the sensors 10 can be separate elements that work in conjunction with and at the direction of various components that form the electrophysiological testing system 30.

As depicted in FIG. 4, the electrophysiological testing system 30 can include a control unit 100. In one embodiment, the control unit 100 can be implemented as a computer system 120 including an analysis program 130, which makes the computer system 120 operable to manage operation of the electrophysiological test system 30, including collection of signals corresponding to the electrical energy sensed by the sensors 10 and any signal processing performed on the signals representative of the electrical energy. In particular, the analysis program 130 can enable the computer system 120 to operate the electrophysiological test system 30 including collecting the signal data generated by the sensors 10 and processing data corresponding to one or more attributes pertaining to a patient 2 on whom the sensors 10 are applied, which can be acquired by the sensors 10, and/or a historical data stored as medical data 140. The processing can result in the generation of additional medical data 140 on the patient 2 from the signal data generated by the sensors 10. The computer system 120 can use the medical data 140 to control one or more aspects of the electrophysiological test applied to the patient 2.

Furthermore, one or more aspects of the electrophysiological test can be controlled or adjusted by a user 4, such as a medical professional, via an external interface input/output component 126B. The external interface input/output component 1266 can be located on the exterior of the electrophysiological testing system 30. The external interface input/output component 126B can include a touch screen that can selectively display user interface controls, such as control dials, which can enable the user 112 to adjust one or more attributes, parameters associated with the electrophysiological test. In an embodiment, the external interface input/output component 126B could conceivably include a keyboard, a plurality of buttons, a joystick-like control mechanism, and/or the like, which can enable the user 112 to control one or more aspects of the operation of the electrophysiological testing system 30. However, it is understood that the external input/output component 126B also can comprise a component which enables interaction with a user 4, which may be physically located remote from the patient 2.

The computer system 120 is shown including a processing component 122 (e.g., one or more processors, signal processing unit), a storage component 124 (e.g., a storage hierarchy), an input/output (I/O) component 126A (e.g., one or more I/O interfaces and/or devices), and a communications pathway 128. In general, the processing component 122 executes program code, such as the analysis program 130, which is at least partially fixed in the storage component 124. While executing program code, the processing component 122 can process data, which can result in reading and/or writing transformed data from/to the storage component 124 and/or the I/O component 126A for further processing. The pathway 128 provides a communications link between each of the components in the computer system 120. The I/O component 126A and/or the external interface I/O component 126B can comprise one or more human I/O devices, which enable a human user 4 to interact with the computer system 120 and/or one or more communications devices to enable a system user 4 to communicate with the computer system 120 using any type of communications link. To this extent, during execution by the computer system 120, the analysis program 130 can manage a set of interfaces (e.g., graphical user interface(s), application program interface, and/or the like) that enable human and/or system users 112 to interact with the analysis program 130. Furthermore, the analysis program 130 can manage (e.g., store, retrieve, create, manipulate, organize, present, etc.) the data, such as medical data 140, using any solution. As used herein, unless otherwise noted, the term "set" means one or more (i.e., at least one) and the phrase "any solution" means any now known or later developed solution.

In any event, the computer system 120 can comprise one or more general purpose computing articles of manufacture (e.g., computing devices) capable of executing program code, such as the analysis program 130, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 130 can be embodied as any combination of system software and/or application software.

Furthermore, the analysis program 130 can be implemented using a set of modules 132. In this case, a module 132 can enable the computer system 120 to perform a set of tasks used by the analysis program 130, and can be separately developed and/or implemented apart from other portions of the analysis program 130. When the computer system 120 comprises multiple computing devices, each computing device can have only a portion of the analysis program 130 fixed thereon (e.g., one or more modules 132). However, it is understood that the computer system 120 and the analysis program 130 are only representative of various possible equivalent monitoring and/or control systems that may perform a process described herein with regard to the control unit. To this extent, in other embodiments, the functionality provided by the computer system 120 and the analysis program 130 can be at least partially be implemented by one or more computing devices that include any combination of general and/or specific purpose hardware with or without program code. In each embodiment, the hardware and program code, if included, can be created using standard engineering and programming techniques, respectively.

Regardless, when the computer system 120 includes multiple computing devices, the computing devices can communicate over any type of communications link. Furthermore, while performing a process described herein, the computer system 120 can communicate with one or more other computer systems, such as the user 4, using any type of communications link. In either case, the communications link can comprise any combination of various types of wired and/or wireless links; comprise any combination of one or more types of networks; and/or utilize any combination of various types of transmission techniques and protocols.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:
1. An electrode sensor comprising:
   a conductive sensor area;
   hydrogel at least partially covering the conductive sensor area, wherein the hydrogel is conductive and includes a surface configured to adhere to skin;

a receptacle forming an open container surrounding the conductive sensor area and the hydrogel, wherein the open container includes a front side with an opening and an opposing back side, the conductive sensor area and the hydrogel placed within the open container, with the surface of the hydrogel configured to adhere to skin facing the opening of the front side, and the conductive sensor area positioned closer to the back side than the hydrogel; and a flange element having a first end affixed near the back side of the container, offset from a plane that is coincident with the surface of the hydrogel, and a second end extending laterally away from the container, wherein a distance between the first end of the flange element and the second end of the flange element is greater than a diameter of at least one of: the back side of the container or the front side of the container.

2. The sensor of claim 1, wherein the receptacle defines an elliptical area.

3. The sensor of claim 1, wherein the receptacle has a decreasing cross-sectional area with an increasing depth.

4. The sensor of claim 1, wherein the receptacle is formed of silicone rubber.

5. The sensor of claim 1, wherein the conductive sensor area is a conductive surface of a snap connector.

6. The sensor of claim 1, wherein the hydrogel comprises silver/silver chloride (Ag/AgCl).

7. The sensor of claim 1, wherein the flange element is formed of flashspun high-density polyethylene fibers.

8. The sensor of claim 1, further comprising a release plate secured over the front side of the open container, wherein the hydrogel is completely enclosed by the conductive sensor area, the receptacle, and the release plate.

9. The sensor of claim 1, wherein a largest diameter of the receptacle is in a range of approximately ten millimeters to approximately twenty millimeters.

10. The sensor of claim 1, wherein the flange element comprises a non-adhesive material.

11. The sensor of claim 1, wherein the first end of the flange element directly contacts the back side of the container.

12. The sensor of claim 1, wherein the flange element is integrated with the container.

13. The sensor of claim 1, wherein the flange element comprises a non-conductive material.

14. An electrophysiological testing system comprising:
a set of electrode sensors, at least one of the set of electrode sensors including:
a conductive sensor area;
hydrogel at least partially covering the conductive sensor area, wherein the hydrogel is conductive and includes a surface configured to adhere to skin of a patient;
a receptacle forming an open container surrounding the conductive sensor area and the hydrogel, wherein the open container includes a front side with an opening and an opposing back side, the conductive sensor area and the hydrogel placed within the open container, with the surface of the hydrogel configured to adhere to skin of the patient facing the opening of the front side, and the conductive sensor area positioned closer to the back side than the hydrogel; and
a flange element having a first end affixed near the back side of the container, offset from a plane that is coincident with the surface of the hydrogel, and a second end extending laterally away from the container, wherein a distance between the first end of the flange element and the second end of the flange element is greater than a diameter of at least one of: the back side of the container or the front side of the container; and
means for collecting signals corresponding to electrical energy sensed by the at least one of the set of electrode sensors.

15. The system of claim 14, wherein the conductive sensor area is a conductive surface of a snap connector.

16. The system of claim 14, further comprising means for processing the signals as part of an electrophysiological test being performed on the patient.

17. An electrode sensor comprising:
a conductive sensor area;
a conductive hydrogel at least partially covering the conductive sensor area, wherein the conductive hydrogel includes a surface configured to adhere to skin;
a receptacle forming an open container surrounding the conductive sensor area and the hydrogel, wherein the open container includes a front side with an opening and an opposing back side, the conductive sensor area and the hydrogel placed within the open container, with the surface of the hydrogel configured to adhere to skin facing the opening of the front side, and the conductive sensor area positioned closer to the back side than the hydrogel;
a first flange element having a first end affixed near the back side of the container, offset from a plane that is coincident with the surface of the hydrogel, and a second end extending away from the container, wherein at least a portion of the first flange element has a width that increases gradually from the first end towards the second end; and
a second flange element having a first end affixed near the back side of the container, offset from the plane that is coincident with the surface of the hydrogel, and a second end extending away from the container, wherein at least a portion of the second flange element has a width that increases gradually from the first end towards the second end, and wherein the second end of the first flange element extends from the container in an opposite direction as the second end of the second flange element.

18. The sensor of claim 17, further comprising a release plate secured over the front side of the open container, wherein the conductive hydrogel is completely enclosed by the conductive sensor area, the receptacle, and the release plate.

19. The sensor of claim 17, wherein the conductive sensor area is a conductive surface of an eyelet of a snap connector, the snap connector including a stud connected to the eyelet, wherein the first flange element and the second flange element are secured between the eyelet and the stud.

20. The sensor of claim 17, wherein the first end of each of the first flange element and the second flange element has a width that approximates a diameter of the opening in the front side of the container, and where each of the first flange element and the second flange element has a tear-drop shape.

* * * * *